(12) United States Patent
Ishizuka et al.

(10) Patent No.: US 11,857,168 B2
(45) Date of Patent: Jan. 2, 2024

(54) IMAGING MODULE, ENDOSCOPE, AND CATHETER

(71) Applicant: Fujikura Ltd., Tokyo (JP)

(72) Inventors: Takeshi Ishizuka, Sakura (JP); Kenichi Ishibashi, Sakura (JP); Daisuke Murakami, Sakura (JP); Yoshinobu Numasawa, Sakura (JP)

(73) Assignee: Fujikura Ltd., Tokyo (JP)

( * ) Notice: Subject to any disclaimer, the term of this patent is extended or adjusted under 35 U.S.C. 154(b) by 767 days.

(21) Appl. No.: 16/967,795

(22) PCT Filed: Jan. 30, 2019

(86) PCT No.: PCT/JP2019/003131
§ 371 (c)(1),
(2) Date: Aug. 6, 2020

(87) PCT Pub. No.: WO2019/159693
PCT Pub. Date: Aug. 22, 2019

(65) Prior Publication Data
US 2023/0200635 A1    Jun. 29, 2023

(30) Foreign Application Priority Data
Feb. 14, 2018    (JP) ................................. 2018-024185

(51) Int. Cl.
*A61B 1/06*    (2006.01)
*A61B 1/04*    (2006.01)
(Continued)

(52) U.S. Cl.
CPC .................. *A61B 1/06* (2013.01); *A61B 1/04* (2013.01); *A61B 1/05* (2013.01); *A61B 1/0661* (2013.01); *A61B 1/07* (2013.01)

(58) Field of Classification Search
CPC ............ A61B 1/05; A61B 1/0661; A61B 1/07
See application file for complete search history.

(56) References Cited

U.S. PATENT DOCUMENTS 6,820,196 B2 * 11/2004 Kessler .............. H04N 21/8166
713/1
8,175,298 B2 * 5/2012 Mitani ..................... H04N 5/60
381/74

(Continued)

FOREIGN PATENT DOCUMENTS

CN         105662319 A    6/2016
JP         H11-253398 A    9/1999
(Continued)

OTHER PUBLICATIONS

International Search Report issued in International Application No. PCT/JP2019/003131, dated May 7, 2019 (5 pages).

*Primary Examiner* — Michael B. Pierorazio
(74) *Attorney, Agent, or Firm* — Osha Bergman Watanabe & Burton LLP (57) ABSTRACT

An imaging module includes: a planar light emitter that includes a light-emitting face and a light-emitter terminal; a power supply cable that is connected to the light-emitter terminal and that supplies electric power to the planar light emitter; a solid-state image sensing device that captures an image of an illumination object that is irradiated with light emitted from the light-emitting face; a coaxial cable that is electrically connected to the solid-state image sensing device; a light shield that is disposed between the solid-state image sensing device and the planar light emitter; and a light guide that guides light emitted from the light-emitting face to an outside of the imaging module. The planar light emitter, the solid-state image sensing device, part of the light shield, and the light guide constitute a rigid portion of the imaging module.

17 Claims, 6 Drawing Sheets

(51) Int. Cl.
  *A61B 1/05*   (2006.01)
  *A61B 1/07*   (2006.01)

(56) References Cited

U.S. PATENT DOCUMENTS

| | | | | |
|---|---|---|---|---|
| 8,201,211 B2* | 6/2012 | Proust | ............... | G06F 21/575 |
| | | | | 707/999.203 |
| 8,351,624 B2* | 1/2013 | Motomura | ....... | H04N 21/43635 |
| | | | | 348/706 |
| 8,838,911 B1* | 9/2014 | Hubin | ............... | H04N 21/2187 |
| | | | | 711/147 |
| 2006/0161958 A1* | 7/2006 | Choung | ............. | H04N 21/4122 |
| | | | | 725/78 |
| 2007/0046835 A1* | 3/2007 | Kim | ............... | H04N 21/485 |
| | | | | 348/731 |
| 2008/0063216 A1* | 3/2008 | Sakata | ............... | H04S 3/008 |
| | | | | 381/80 |
| 2008/0309830 A1* | 12/2008 | Motomura | ....... | H04N 21/43635 |
| | | | | 348/E5.122 |
| 2008/0320545 A1* | 12/2008 | Schwartz | ........... | H04N 21/8541 |
| | | | | 725/135 |
| 2009/0012366 A1* | 1/2009 | Wang | ............... | A61B 1/05 |
| | | | | 600/178 |
| 2010/0315553 A1* | 12/2010 | Takatsuji | ............... | G09G 5/006 |
| | | | | 348/E9.034 |
| 2010/0321479 A1* | 12/2010 | Yang | ............... | H04N 21/816 |
| | | | | 348/51 |
| 2011/0033973 A1* | 2/2011 | Cok | ............... | C23C 14/243 |
| | | | | 118/726 |
| 2011/0051002 A1* | 3/2011 | Oh | ............... | H04N 5/765 |
| | | | | 348/569 |
| 2011/0068736 A1* | 3/2011 | Chartier | ............... | H02J 7/00 |
| | | | | 320/137 |
| 2011/0113442 A1* | 5/2011 | Kikkawa | ............... | G09G 5/006 |
| | | | | 725/25 |
| 2011/0134338 A1* | 6/2011 | Toba | ............... | H04N 5/765 |
| | | | | 348/734 |
| 2011/0142245 A1* | 6/2011 | Toba | ............... | H04N 21/436 |
| | | | | 381/22 |
| 2011/0176057 A1* | 7/2011 | Okamura | ............. | H04N 21/439 |
| | | | | 348/554 |
| 2011/0234916 A1* | 9/2011 | Fujita | ............... | H04N 5/60 |
| | | | | 348/E5.122 |
| 2012/0002562 A1* | 1/2012 | Kawade | ............... | H04N 5/765 |
| | | | | 370/252 |
| 2012/0030728 A1* | 2/2012 | Yukawa | ............... | G06F 9/44 |
| | | | | 725/151 |
| 2012/0042346 A1* | 2/2012 | Yoshida | ............. | H04N 21/4363 |
| | | | | 725/81 |
| 2012/0136612 A1* | 5/2012 | Vanderhoff | .......... | H04N 17/004 |
| | | | | 702/119 |
| 2012/0188456 A1* | 7/2012 | Kuroyanagi | ........... | H04N 5/765 |
| | | | | 348/731 |
| 2012/0307157 A1* | 12/2012 | Utsunomiya | .... | H04N 21/43622 |
| | | | | 348/707 |
| 2013/0021536 A1* | 1/2013 | Kamida | ........... | H04N 21/43622 |
| | | | | 348/739 |
| 2013/0051578 A1* | 2/2013 | Chu | ............... | H04B 1/123 |
| | | | | 381/94.1 |
| 2013/0051584 A1* | 2/2013 | Higuchi | ............. | H04N 21/8106 |
| | | | | 381/123 |
| 2013/0223538 A1* | 8/2013 | Wang | ............... | H04N 21/43637 |
| | | | | 375/E7.027 |
| 2013/0292311 A1* | 11/2013 | Shaw | ............... | E03F 5/042 |
| | | | | 137/15.01 |
| 2014/0193134 A1* | 7/2014 | Maeda | ............. | H04N 21/43072 |
| | | | | 386/231 |
| 2015/0077633 A1* | 3/2015 | Lee | ............... | H04N 21/4392 |
| | | | | 348/515 |
| 2015/0157194 A1* | 6/2015 | Okuda | ............... | A61B 1/00197 |
| | | | | 600/109 |
| 2016/0029879 A1* | 2/2016 | Ishikawa | ............... | A61B 1/005 |
| | | | | 600/110 |
| 2016/0150945 A1* | 6/2016 | Okamoto | ........... | A61B 1/00101 |
| | | | | 600/114 |
| 2017/0196537 A1* | 7/2017 | Saiga | ............... | A61B 8/461 |

FOREIGN PATENT DOCUMENTS

| | | |
|---|---|---|
| JP | 2007-021084 A | 2/2007 |
| JP | 2008-212309 A | 9/2008 |
| JP | 2012-205849 A | 10/2012 |
| JP | 2017-099530 A | 6/2017 |

* cited by examiner

IMAGING MODULE, ENDOSCOPE, AND CATHETER

CROSS-REFERENCE TO RELATED APPLICATIONS

This application claims priority from Japanese Patent Application No. 2018-024185 filed on Feb. 14, 2018, the contents of which are incorporated herein by reference in their entirety.

TECHNICAL FIELD

The present invention relates to an imaging module, an endoscope, and a catheter.

BACKGROUND

Conventionally, an endoscope including a light guide fiber bundle for illumination is known (for example, refer to Patent Document 1). In the endoscope, a fiber bundle is disposed so as not to interfere with an imaging module that is configured of a solid-state image sensing device, an image sensing device holding tube, or the like, and a space between optical fibers constituting the fiber bundle is filled with a low-viscosity adhesive. A light source that supplies light to the fiber bundle is provided at the rear of the endoscope, and light emitted from the light source is guided to the distal end of the endoscope via the fiber bundle.

PATENT LITERATURE (Patent Literature 1) Japanese Unexamined Patent Application, First Publication No. 2008-212309

However, there are the following issues in the endoscope including the light guide fiber bundle. The fiber bundle has rigidity and therefore cannot be sufficiently bent. Accordingly, by use of the fiber bundle in an endoscope, flexibility in the endoscope is degraded. In a case where an optical fiber is broken due to bending of the fiber bundle, light from a light source cannot be guided to the distal end of the fiber bundle. It is necessary to increase the numbers of optical fibers constituting the fiber bundle in order to obtain sufficient illuminance; in this case, the cross-sectional area of the fiber bundles increases, and providing an endoscope with a small diameter is therefore not possible. Since the fiber bundle is arranged in the entire length of the endoscope, a working channel having a sufficient size in a plane of projection of the endoscope cannot be ensured. Additionally, the material costs and the assembling costs of the fiber bundle increase, and providing an inexpensive endoscope is not possible.

SUMMARY

One or more embodiments of the present invention provide an imaging module that has a small diameter and can achieve an endoscope that obtains sufficient flexibility and illuminance, an endoscope including the imaging module, and a catheter including the imaging module.

An imaging module according to one or more embodiments of the present invention includes: a planar light emitter that includes a light-emitting face and a light-emitter terminal; a power supply cable that is connected to the light-emitter terminal of the planar light emitter and supplies electric power to the planar light emitter; a solid-state image sensing device that captures an image of an illumination object to be irradiated with light emitted from the light-emitting face of the planar light emitter; a coaxial cable that is electrically connected to the solid-state image sensing device; a light-shielding member (i.e., light shield) that is provided between the solid-state image sensing device and the planar light emitter; and a light guide that guides light emitted from the light-emitting face of the planar light emitter to an outside of the imaging module, wherein the planar light emitter, the solid-state image sensing device, part of the light-shielding member, and the light guide constitute a rigid portion.

The imaging module according to one or more embodiments of the present invention may further include a connector that is located between the solid-state image sensing device and the coaxial cable and that includes: a main body formed of an insulating member (i.e., insulator); and an implanted conductor that is provided inside the main body and electrically connects the solid-state image sensing device and the coaxial cable.

In the imaging module according to one or more embodiments of the present invention, the connector may include a side-face terminal at which the implanted conductor is exposed to an inside of a groove formed on a side face of the main body, the coaxial cable may be electrically connected to the side-face terminal, and the planar light emitter may be disposed so as to be adjacent to the coaxial cable in a rear region facing the coaxial cable at a rear of the connector.

The imaging module according to one or more embodiments of the present invention may further include a lens unit that causes reflected light from the illumination object to be formed as an image on a light-receiving face of the solid-state image sensing device, wherein the planar light emitter may be disposed adjacent to the lens unit or to the solid-state image sensing device.

In the imaging module according to one or more embodiments of the present invention, the power supply cable may include an electrical wire connected to the light-emitter terminal, an electrical-wire front end of the electrical wire may be brought into contact with the light-emitter terminal, and solder may be formed so as to cover a contact portion between the light-emitter terminal and the electrical-wire front end.

In the imaging module according to one or more embodiments of the present invention, the light-emitter terminal may include a terminal outer periphery located at an end of the light-emitter terminal, the electrical wire may include a side surface portion located at a position apart from the electrical-wire front end, and the solder may coat the light-emitter terminal and the electrical wire so as to form a curved surface extending from the terminal outer periphery toward the side surface portion.

In the imaging module according to one or more embodiments of the present invention, the power supply cable may include a shield member (i.e., shield) coating an outer side of the electrical wire.

In the imaging module according to one or more embodiments of the present invention, the power supply cable may be an ultrafine coaxial cable.

In the imaging module according to one or more embodiments of the present invention, the light-emitter terminal and the power supply cable may be coated with a cable reinforcing portion.

In the imaging module according to one or more embodiments of the present invention, the light-shielding member may be formed of a material having a light shielding property.

The imaging module according to one or more embodiments of the present invention may further include a light guide plate provided on an end face of the light guide.

In the imaging module according to one or more embodiments of the present invention, an end face of the light guide may coincide with an end face of the imaging module.

In the imaging module according to one or more embodiments of the present invention, a plurality of the planar light emitters may be provided, and the plurality of the planar light emitters may be arranged so as to sandwich the solid-state image sensing device in plan view.

In the imaging module according to one or more embodiments of the present invention, a plurality of the planar light emitters may be provided, and the plurality of the planar light emitters may be arranged so as to surround the solid-state image sensing device in plan view.

The imaging module according to one or more embodiments of the present invention may further include a housing that covers an outer side of the light-shielding member.

An endoscope according to one or more embodiments of the present invention includes the imaging module according to one or more embodiments.

A catheter according to one or more embodiments of the present invention includes: the imaging module according to one or more embodiments; a tube that surrounds the imaging module and has an insulation property; and a channel provided in the tube.

As described above, according to the above-mentioned embodiments, it is possible to provide an imaging module that has a small diameter and can achieve an endoscope that obtains sufficient flexibility and illuminance. Furthermore, it is possible to provide an ultrafine endoscope and a catheter which obtain sufficient flexibility and illuminance.

DETAILED DESCRIPTION

Hereinafter, embodiments of the present invention will be described with reference to drawings.

In the drawings showing embodiments of the invention, in order for the respective components to be of understandable size in the drawings, the dimensions and the proportions of the components are modified as needed compared with the real components.

Endoscope 100

Figure 1:
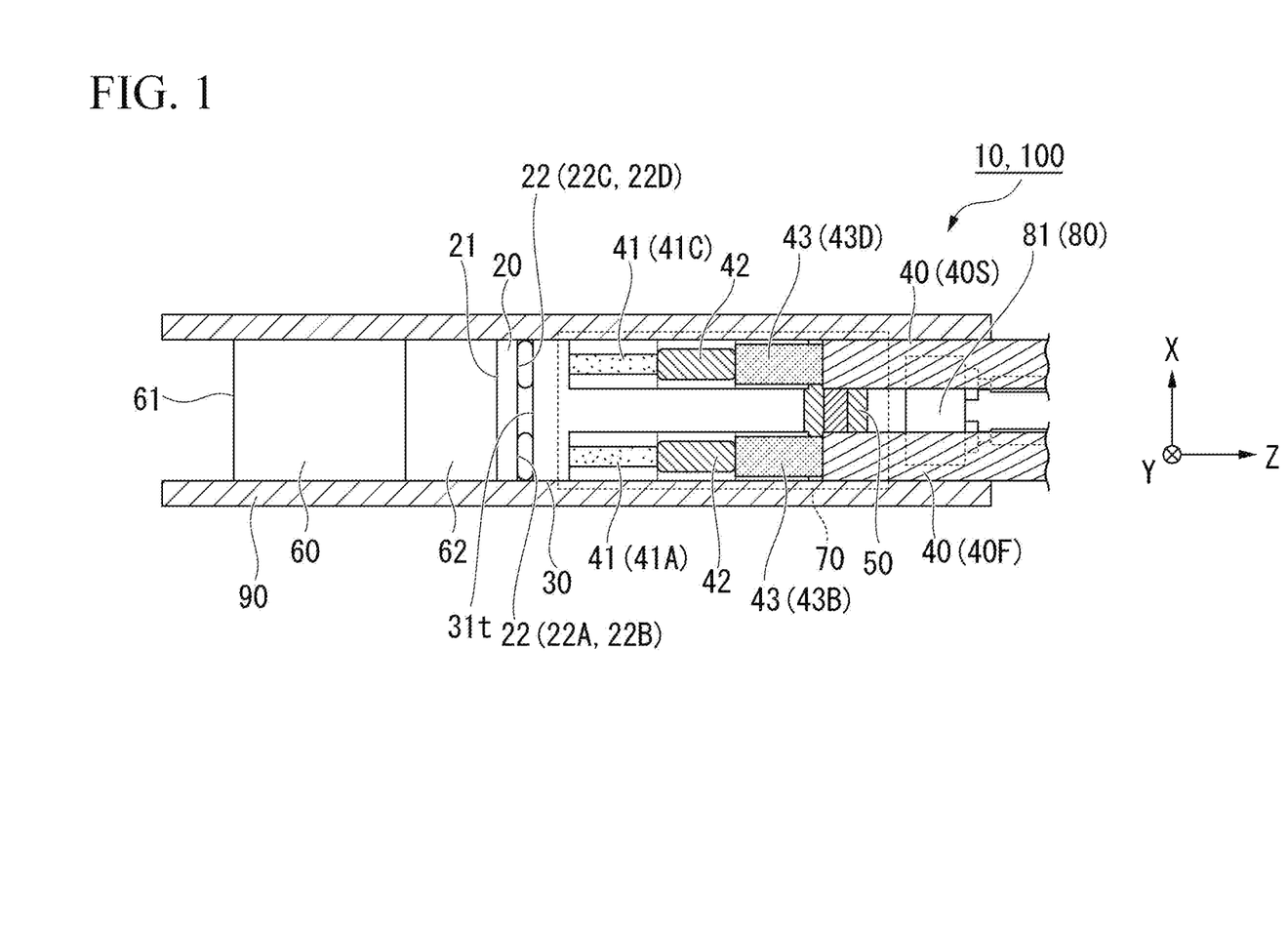
FIG. 1 is a view showing a relevant part of an endoscope according to one or more embodiments of the present invention and is a cross-sectional view showing a configuration of an imaging module.
Figure 2:
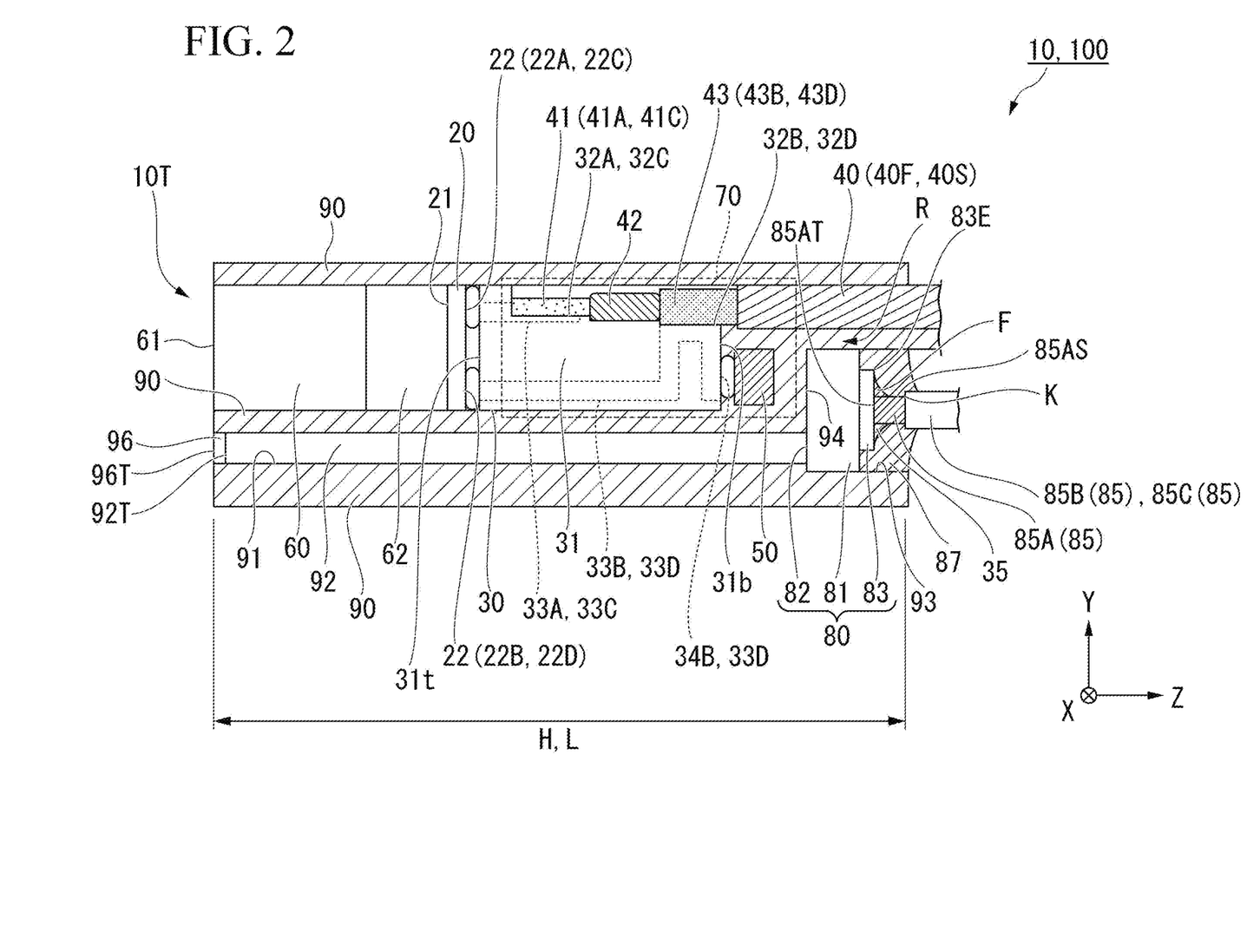
FIG. 2 is a view showing a relevant part of the endoscope according to one or more embodiments of the present invention and a cross-sectional view showing the configuration of the imaging module.

FIGS. 1 and 2 are views showing a relevant part of an endoscope 100 according to one or more embodiments of the present invention and are cross-sectional views showing a configuration of an imaging module 10. Particularly, FIG. 1 is a cross-sectional view as seen in the Y-direction, and FIG. 2 is a cross-sectional view as seen in the X-direction.

In the following explanation, in the Z-direction, the direction from a connector 30 to the solid-state image sensing device 20 (left side in FIG. 1) may be referred to as "forward" or "front side". The direction from the connector 30 to coaxial cables 40 (right side in FIG. 1) may be referred to as "rear" or "back side".

Imaging Module 10

The imaging module 10 includes: the solid-state image sensing device 20 (image sensor); the connector 30, two coaxial cables 40 (first coaxial cable 40F and second coaxial cable 40S); a capacitor 50 (electronic component); a lens unit 60; an insulating tube 70; a light-emitting diode 80; and a light-shielding member (i.e., light shield) 90.

Solid-State Image Sensing Device 20

The solid-state image sensing device 20 is provided in front of the connector 30.

The solid-state image sensing device 20 includes: a light-receiving face 21 located on an upper face of the solid-state image sensing device 20; and four image-sensing terminals 22 (22A, 22B, 22C, 22D) which are provided on a lower face of the solid-state image sensing device 20. The lens unit 60 is mounted on the light-receiving face 21. The image-sensing terminals 22 is a terminal connected to mounting pads (described below) provided on an upper face 31t of the connector 30. As the solid-state image sensing device 20, for example, a CMOS (complementary metal oxide semiconductor) may be used.

In the imaging module 10, the solid-state image sensing device 20 is electrically connected to the two coaxial cables 40 via the connector 30.

Connector 30

The connector 30 is located between the solid-state image sensing device 20 and the coaxial cables 40.

The connector 30 includes: a main body 31 formed of an insulating member (i.e., insulator); and implanted conductors 33A and 33C (first implanted conductor) and implanted conductors 33B and 33D (second implanted conductor) which are provided inside the main body 31.

Grooves that are partially removed from the connector 30 are formed on a side face of the main body 31. The implanted conductors 33A and 33C at which side-face terminals 32A and 32C (first side-face terminal) are exposed, respectively, and the implanted conductors 33B and 33D at which side-face terminals 32B and 32D (second side-face terminal) are exposed, respectively, are provided inside the grooves.

Lower face terminals 34B and 34D at which the implanted conductors 33B and 33D are exposed are provided on a lower face 31b of the main body 31.

The implanted conductors 33A, 33B, 33C, and 33D are electrically connected to the image-sensing terminals 22A, 22B, 22C, and 22D, respectively, via mounting pads provided on the upper face 31t of the connector 30.

The lengths (in the X-direction and the Y-direction) of one side of the upper face 31t of the connector 30 are less than or equal to 2 mm.

Coaxial Cable 40

As shown in FIG. 1, the imaging module 10 includes the two coaxial cables 40 (40F and 40S). Each of the coaxial cables 40 includes: an internal conductor 41 (41A and 41C); a coating portion 42 (insulator), and a sheath conductor 43 (43B and 43D). Specifically, the coaxial cable 40F includes the internal conductor 41A and the sheath conductor 43B. The coaxial cable 40S includes the internal conductor 41C and the sheath conductor 43D.

A length of the internal conductor 41, a length of the sheath conductor 43, and a length of the coating portion 42 located between the internal conductor 41 and the sheath conductor 43 are each 0.1 to 1.0 mm.

The internal conductor 41, the coating portion 42, and the sheath conductor 43 of the coaxial cables 40 are disposed inside the grooves of the connector 30. The internal conductor 41A is electrically connected to the side-face terminal 32A by soldering. The sheath conductor 43B is electrically connected to the side-face terminal 32B by soldering. The internal conductor 41C is electrically connected to the side-face terminal 32C by soldering. The sheath conductor 43D is electrically connected to the side-face terminal 32D by soldering.

According to the aforementioned connection structure, the image-sensing terminal 22A of the solid-state image sensing device 20 is electrically connected to the internal conductor 41A via the implanted conductor 33A. The image-sensing terminal 22B of the solid-state image sensing device 20 is electrically connected to the sheath conductor 43B via the implanted conductor 33B.

The image-sensing terminal 22C of the solid-state image sensing device 20 is electrically connected to the internal conductor 41C via the implanted conductor 33C. The image-sensing terminal 22D of the solid-state image sensing device 20 is electrically connected to the sheath conductor 43D via the implanted conductor 33D.

Capacitor 50

The capacitor 50 is mounded on the lower face 31b of the connector 30 via mounting pads. External terminals of the capacitor 50 are connected to the lower face terminals 34B and 34D. Note that, a resin layer is provided on the lower face 31b of the connector 30 and short-circuiting between the lower face terminals 34B and 34D is prevented.

Lens Unit 60

The lens unit 60 has a configuration in which an object lens (not shown in the drawings) is incorporated into a cylindrical lens barrel (not shown in the drawings). The optical axis of the lens unit 60 is positionally-fixed on the light-receiving face 21 of the solid-state image sensing device 20. One end of the lens barrel in the axis direction is fixed to a cover member 62. Light that is incident to an imaging surface 61 located in front of the lens unit 60 through the lens provided inside the lens barrel and is thereby guided is provided as an image on the light-receiving face 21 of the solid-state image sensing device 20 by the lens unit 60.

Insulating Tube 70

The insulating tube 70 is a resin tube with electrical insulation. As the insulating tube 70, a heat shrinkable tube is used. As a material used to form the insulating tube 70, for example: polyimide resin; silicone resin; polyolefin resins such as polyethylene terephthalate (PET) resin, nylon resin, polyethylene resin, or polypropylene resin; or fluorine resins such as polytetrafluoroethylene (PTFE) resin is used.

The insulating tube 70 coves at least one of: the connector 30; and part of the coaxial cables 40 which are connected to the connector 30. In one or more embodiments in which the capacitor 50 is connected to the connector 30, the insulating tube 70 collectively covers the connector 30, part of the coaxial cables 40, and the capacitor 50. Here, the part of the coaxial cables 40 means the region including: the internal conductor 41, the coating portion 42, and not only the region (exposed region) on which the sheath conductor 43 is formed but also an outer coating (the portion coating the sheath conductor 43) that is located close to the connector 30.

As shown in FIG. 1, the insulating tube 70 according to one or more embodiments covers the coaxial cables 40 so as to protrude from the end of the capacitor 50 toward the outside (right side). With this configuration, the insulating tube 70 protects the connector 30, the coaxial cables 40, and the capacitor 50, and can achieve a high insulation property.

Light-Emitting Diode 80

The light-emitting diode 80 includes: a light emitter 81 (planar light emitter) configured of a flat plate having a thickness of approximately 0.25 mm; a light-emitting face 82 that is a flat surface located in front of the light emitter 81; and light-emitter terminals 83 that are provided on a surface (surface on the opposite side of the light-emitting face 82) located at the back side of the light emitter 81. The light-emitter terminals 83 are electrically connected to a power supply cable 85 which will be described later.

In one or more embodiments, for example, a surface-mounted light emitting diode is applied as the light-emitting diode 80. Consequently, light having straightness can be emitted from the light-emitting face 82, and it is possible to ensure sufficient illuminance.

In other cases, as long as straightness of light is reliably obtained, the light emitting diode is not limited to a surface-mounted light emitting diode, and a light-emitting diode having the other configuration may be applied to one or more embodiments of the present invention.

The light-emitting diode 80 is disposed at a rear region R which faces the capacitor 50 and the coaxial cables 40 at the rear of the connector 30. More specifically, the light-emitting diode 80 is disposed so as to be adjacent to the coaxial cables 40 and so that part of the light-emitting face 82 of the light-emitting diode 80 and the capacitor 50 face each other. In other words, at the back side of the connector 30, the light-emitting diode 80 is disposed at the rear region R at which the coaxial cables 40 are not disposed.

Note that, an example in which the capacitor 50 is provided on the lower face 31b of the connector 30 is explained in one or more embodiments; however, the light-emitting diode 80 is disposed at the rear region R so that part of the light-emitting face 82 faces the lower face 31b in the configuration in which the capacitor 50 is not provided.

The power supply cable 85 includes: an electrical wire 85A; an outer coating 85B that coats the electrical wire 85A; and a shield member (i.e., shield) 85C that coats the outer coating 85B. The electrical wire 85A supplies electric power to the light-emitter terminals 83 from a power supply which is not shown in the drawings. The outer coating 85B is an insulating coating that provides insulation property to the surface of the electrical wire 85A. The shield member 85C coats the outer coating 85B, that is, coats the outside of the electrical wire 85A. The shield member 85C is formed of a metal member such as a metallic mesh and inhibits noise due to the power supply to the electrical wire 85A from affecting the coaxial cables 40. The outer-periphery of the shield member 85C is coated with an insulation material. In other cases, the power supply cable 85 may be an ultrafine coaxial cable.

The power supply cable 85 is configured of two cables that apply a voltage to the light-emitting diode 80. Each of the two cables includes the electrical wire 85A and the outer coating 85B. The shield member 85C may have a configuration that coats the outer coating 85B of each of the two cables or may have a configuration that collectively coats two outer coating 85B of the two cables.

In other cases, the shield member 85C is not necessarily required to be provided, and a configuration that does not include the shield member 85C may be adopted.

The electrical wire 85A is exposed by removing the outer coating 85B of the power supply cable 85, the exposed electrical wire 85A is brought into contact with the light-emitter terminal 83 and is soldered by use of solder 35. Particularly, the electrical-wire front end 85AT of the electrical wire 85A is brought into contact with the light-emitter terminal 83, and the solder 35 is formed so as to coat a contact portion between the light-emitter terminal 83 and the electrical-wire front end 85AT.

On the solder 35 formed on the light-emitter terminal 83, a curved surface F (fillet shape) may be formed on the surface of the solder 35.

The shape of the curved surface F can be adequately adjusted depending on an amount of the solder 35 that is supplied to the surface of the light-emitter terminal 83. The shape of the curved surface F is not limited to the shape shown in FIG. 2.

Particularly, the light-emitter terminal 83 has a terminal outer periphery 83E that is located at the end (the position apart from the electrical wire 85A) of the light-emitter terminal 83. The electrical wire 85A has a side surface portion 85AS that is located at the position apart from the electrical-wire front end 85AT. The solder 35 coats the light-emitter terminal 83 and the electrical wire 85A so as to form the curved surface F that extends from the terminal outer periphery 83E toward the side surface portion 85AS.

Here, the position of the side surface portion 85AS in the Z-direction shown in FIG. 2 is the position apart from the light-emitter terminal 83 and is located near a boundary K between the electrical wire 85A and the outer coating 85B. Alternatively, the side surface portion 85AS may coat the boundary K between the electrical wire 85A and the outer coating 85B.

The light-emitter terminal 83 and the power supply cable 85 are fixed by a cable reinforcing portion 87 inside a light-emitting diode insertion hole 93 which will be described later. On the lower face of the light-emitting diode 80, the cable reinforcing portion 87 coats the light-emitter terminal 83, the solder 35, and the power supply cable 85.

Accordingly, connection strength between the light-emitter terminal 83 and the power supply cable 85 increases.

The power supply cable 85 is connected to a power supply which is not shown in the drawings. Electric power output from the power supply is supplied to the light-emitting diode 80 via the power supply cable 85. In other words, electric power is supplied to the light-emitting diode 80 via a cable different from the coaxial cables 40. The power supply cable 85 is softer than optical fibers constituting the fiber bundle used in a conventional endoscope and has flexibility.

Light-Shielding Member 90

The light-shielding member 90 is provided between the solid-state image sensing device 20 and the light-emitting diode 80 and, particularly in one or more embodiments, covers the entire body constituting the imaging module 10, i.e., the solid-state image sensing device 20, the connector 30, the coaxial cables 40, the capacitor 50, the lens unit 60, the insulating tube 70, and the light-emitting diode 80. That is, the light-shielding member 90 holds the entire body constituting the imaging module 10 in an integrated manner.

In an example shown in FIG. 2, the length of the light-shielding member 90 in the Z-direction is set to the length of a rigid portion H which will be described later (rigid-portion length L). The length of the light-shielding member 90 is not limited to the example shown in FIG. 2 and may be shorter than the rigid-portion length L.

Two through holes, that is, a light guiding hole 91 and the light-emitting diode insertion hole 93 are provided on the light-shielding member 90. Furthermore, a step difference formed between the light-emitting diode insertion hole 93 and the light guiding hole 91, that is, a butt joint portion 94 is provided inside the light-emitting diode insertion hole 93. The butt joint portion 94 is located at the rear region R.

Part of the light-emitting face 82 is exposed to the inside of the light guiding hole 91. A light guide 92 extending in the Z-direction is provided inside the light guiding hole 91. Light emitted from the light-emitting face 82 of the light-emitting diode 80 is guided to the outside of the imaging module 10 by the light guide 92.

The light guide 92 is a transparent resin which is obtained by curing liquid resin having flowability, is fixed in the inside of the light guiding hole 91, and does not have bendability. Moreover, the material of the light guide 92 is not limited to a resin but may be an optical fiber. Particularly, the light guiding hole 91 and the light guide 92 serves as an optical path.

In other cases, the inside of the light guiding hole 91 may be a space. That is, the light guide 92 may be a light guide member provided inside the light guiding hole 91 or may be a space. However, in order to obtain straightness of the light emitted from the light-emitting face 82, the light guide 92 may be disposed inside the light guiding hole 91.

A reflection surface that reflects light may be formed on an inner surface of the light guiding hole 91.

Moreover, the light guiding hole 91 may be a metal tube such as stainless steel (SUS) which is implanted in the light-shielding member 90. In this case, the metal tube serves as a light-shielding member, and the metal tube is fixed adjacent to the lens unit 60, the solid-state image sensing device 20, and the connector 30 with resin or the like.

A flat plate-shaped light guide plate 96 is provided on the end face 92T in front of the light guide 92. In the Z-direction, the end face 96T of the light guide plate 96 coincides with the imaging surface 61 of the lens unit 60, that is, coincides with the end face 10T of the imaging module 10.

The light guide plate 96 is formed of a transparent resin having a high light transparency, and is a resin plate formed of, for example, polycarbonate or the like. Alternatively, the light guide plate 96 may be a member which is cured after the recessed portion surrounded by part of the light guiding hole 91 and the end face 92T is filled with liquid adhesive.

The light guide plate 96 may serve as a protection cover (protector) that protects the light-emitting diode 80. Additionally, the light guide plate 96 may serve as a lens (optical member) that refracts light guided by the light guide 92. Moreover, the light guide plate 96 may serve as a light diffusion plate (optical member) that diffuses light guided by the light guide 92 toward the outside of the light guide plate 96.

In a case where the imaging module 10 according to one or more embodiments is applied to an endoscope for observation of a living body, the light guide plate 96 may serve as an adherence prevention member that prevents fluid of the living body from being attached to the imaging module 10. In addition, the light guide plate 96 may be formed of a material with biological compatibility.

The light-emitting diode insertion hole 93 is a hole through which the light-emitting diode 80 passes toward from the rear to the inside of the light-shielding member 90 when the light-emitting diode 80 is attached to the inside of the light-shielding member 90. Inside the light-emitting diode insertion hole 93, the light-emitting diode 80 comes into contact with the butt joint portion 94 and is fixed thereto by a known fixing member such as adhesive or the like. In the above-described fixation configuration, part of the light-emitting face 82 comes into contact with the butt joint portion 94 and is fixed thereto.

Reference letter H represents the portion that does not bend in the imaging module 10, that is, the rigid portion H.

The rigid portion H only has to be configured of at least the light-emitting diode 80, the solid-state image sensing device 20, and part of the light-shielding member 90. In one or more embodiments, the rigid portion H is configured of the light-emitting diode 80, the lens unit 60, the solid-state image sensing device 20, part of the light-shielding member 90, the connector 30, and part of the coaxial cables 40. The length of the rigid portion H, that is, the rigid-portion length L is, for example, approximately 5 mm.

As the constituent material of the light-shielding member 90, a known resin having light shielding property such as epoxy resin, acrylic resin, urethane resin, or the like may be adopted. Furthermore, the light-shielding member 90 may be formed using a material having a known resin and carbon black that is added thereto.

In one or more embodiments, the light-shielding member 90 is provided so as to cover the solid-state image sensing device 20, the lens unit 60, the connector 30, and the light-emitting diode 80; however, the invention is not limited to a configuration of the light-shielding member 90. By providing the light-shielding member 90 at the periphery of the solid-state image sensing device 20 and the lens unit 60, the emitted light of the light-emitting diode 80 may be prevented from being incident to the solid-state image sensing device 20 and the lens unit 60. The light-shielding member 90 may have not only a light-shielding function but also a function of the insulating tube 70 which will be described later. In this case, it is not necessary to provide the insulating tube 70.

Light emitted from the light-emitting diode 80 is emitted to the outside of the imaging module 10 through the light guide 92. Moreover, the emitted light of the light-emitting diode 80 is prevented from being incident to the solid-state image sensing device 20 by the light-shielding member 90.

Next, an action of the endoscope 100 including the imaging module 10 configured described above will be described.

When electric power is supplied to the light-emitting diode 80 via the power supply cable 85, the light-emitting diode 80 emits light, and the light emitted from the light-emitting diode 80 exits to the outside the imaging module 10 through the light guide 92. The light illuminates an illumination object to be observed by the endoscope 100, and the reflected light from the illumination object (image) enters the imaging surface 61 of the lens unit 60. The light (image) that is incident to the lens unit 60 is formed as an image on the light-receiving face 21 of the solid-state image sensing device 20 by the object lens. Therefore, the solid-state image sensing device 20 captures an image of the illumination object as an image and outputs the obtained image as electrical signals. The signals output from the solid-state image sensing device 20 are received by a control device provided outside the imaging module 10 through the coaxial cables 40.

In the aforementioned imaging module 10 according to one or more embodiments, since the power supply cable 85 is softer than an optical fiber and has sufficient flexibility, it is possible to achieve an imaging module having an excellent flexibility more than that of a fiber bundle configured of optical fibers. Moreover, since it is possible to emit the light emitted from the light-emitting diode 80 to the outside of the imaging module 10, it is possible to achieve the endoscope 100 that can obtain sufficient illuminance.

Since the power supply cable 85 is finer than a conventional fiber bundle, it is possible to achieve the imaging module 10 with a small diameter, that is, it is possible to achieve the endoscope 100 with a small diameter.

In one or more embodiments, the coaxial cables 40F and 40S are connected to the side-face terminals 32A, 32B, 32C, and 32D provided inside the grooves formed on a side face of the main body 31 of the connector 30. With this configuration, the rear region R at which the coaxial cables are not disposed can be obtained at the back side of the connector 30, and the light-emitting diode 80 can be disposed at the rear region R.

Accordingly, regarding the arrangement layout of the components constituting the imaging module 10, it is possible to effectively use the rear region R as the position at which the light-emitting diode 80 is disposed. That is, as compared with a configuration in which a coaxial cable is disposed at the back side of the connector 30, the light-emitting diode 80 can be disposed to be close to the coaxial cables 40F and 40S in the directions (in the Y-direction in the case of FIG. 2) perpendicular to the Z-direction. Consequently, the imaging module 10 with a small diameter can be achieved, that is, it is possible to achieve the endoscope 100 with a small diameter.

Since a surface-mounted light emitting diode that is a flat plate having a thin thickness in the Z-direction is applied to the imaging module 10 as the light-emitting diode 80, it is possible to shorten the rigid-portion length L.

Additionally, the light guide 92 is fixed to the inside of the light guiding hole 91 in the rigid portion H, and the light guide 92 is prevented from being bent. Therefore, the light guide 92 is not damaged due to the bending.

In the connection structure between the light-emitting diode 80 and the power supply cable 85, as the power supply cable 85 with the electrical wire 85A is applied to the surface-mounted light emitting diode, the material costs and the assembling costs can be reduced.

Since the power supply cable 85 is finer than a fiber bundle, as a result of applying the imaging module 10 including the power supply cable 85 to an endoscope or catheter, it is possible to ensure a working channel having a sufficient size in a plane of projection.

Since the power supply cable 85 includes the shield member 85C, it is possible to inhibit noise due to the power supply to the electrical wire 85A from affecting the coaxial cables 40.

As the curved surface F is formed on the solder 35, the surface area of the solder 35 increases, and radiation performance of the light-emitting diode 80 is improved. Particularly, a coefficient of thermal conductivity of resin is approximately 0.5 W/mK, by contrast, coefficients of thermal conductivity of solder and an electrical wire are greater than or equal to 10 W/mK. In a conventional configuration in which a light-emitting diode is coated with resin or the like, heat generation from the light-emitting diode stays inside the resin, heat radiation is less likely to occur.

By contrast, in the imaging module 10 according to one or more embodiments, as the surface area of the solder 35 having a coefficient of thermal conductivity higher than that of resin increases, excellent radiation performance more than a conventional case is obtained.

Furthermore, since the electrical wire 85A is directly connected to the light-emitter terminal 83, heat radiation of the light-emitting diode 80 can be sufficiently carried out. Moreover, as the curved surface F is formed on the solder 35, the reliability of electrical connection between the light-emitter terminal 83 and the electrical wire 85A is improved.

Since the electrical-wire front end 85AT of the electrical wire 85A is brought into contact with the light-emitter terminal 83 and the electrical wire 85A is soldered to the light-emitter terminal 83, the surface area of the portion to be soldered becomes small, thereby contributing to achievement of the imaging module 10 with a small diameter.

For example, although the surface area of the portion to be soldered becomes large in the case of soldering a bent portion of a folded electrical wire to a light-emitter terminal, it is possible to reduce the surface area to be soldered in one or more embodiments.

In the connection structure between the light-emitting diode 80 and the power supply cable 85, it is necessary to check whether or not the light-emitter terminal 83 of the light-emitting diode 80 is reliably connected to the electrical wire 85A of the power supply cable 85 (connected state). In this case, by observing the light-emitter terminal 83 and thereby determining whether or not the solder 35 has the curved surface F on the light-emitter terminal 83, a connected state between the light-emitter terminal 83 and the electrical wire 85A can be easily determined.

Modified Examples

Next, modified examples of the above-mentioned embodiments will be described.

In the modified examples described below, identical symbols are used for the elements which are identical to those of one or more embodiments, and the explanations thereof are omitted or simplified here.

Modified Example 1

Although the connector 30 having the configuration in which the coaxial cables 40 are electrically connected to the side-face terminals 32A, 32B, 32C, and 32D exposed at the grooves of the connector 30 is described in the above-described embodiments, the invention is not limited to the configuration of the connector 30.

For example, exposed terminals at which the implanted conductors 33A, 33B, 33C, and 33D are exposed are provided on the lower face 31b of the connector 30, and the coaxial cables 40 may be electrically connected to the exposed terminals.

In this case, the rear region R is not formed. The light-emitting diode 80 is disposed so as to be adjacent to any one of the solid-state image sensing device 20, the connector 30, and the coaxial cables 40 in the X-direction or the Y-direction.

In this configuration, the wiring structure inside the connector becomes simple, and it is possible to shorten the length of the connector in the Z-direction. Because of this, it is possible to shorten the rigid-portion length L of the imaging module including the light-emitting diode 80.

In addition, the configuration in which the connector 30 is omitted, that is, the configuration in which the solid-state image sensing device 20 are directly connected to the coaxial cables 40 may be adopted. In this case, the light-emitting diode 80 is disposed so as to be adjacent to any one of the solid-state image sensing device 20 and the coaxial cables 40 in the X-direction or the Y-direction. Similar to the above description, it is possible to shorten the rigid-portion length L of the imaging module including the light-emitting diode 80. In the modified examples 2 and 3 described below, a configuration in which the light-emitting diode 80 is adjacent to the lens unit 60 in the Y-direction will be described.

Modified Examples 2 and 3

Figure 3A:
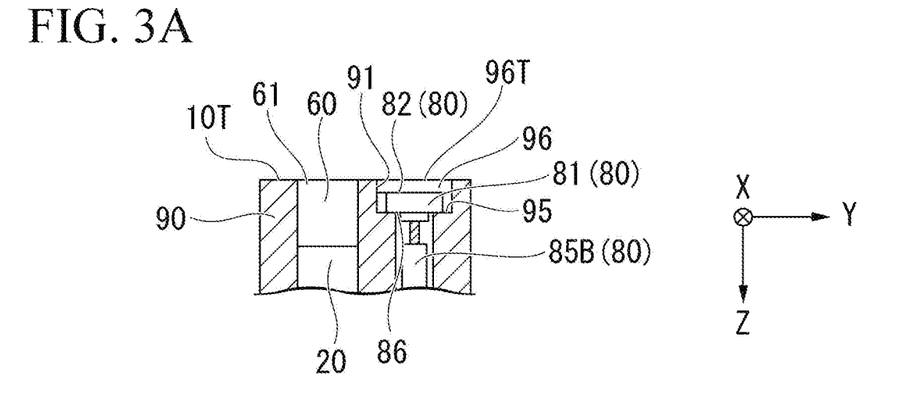
FIG. 3A is a view showing a relevant part of an endoscope according to a modified example 2 of one or more embodiments of the present invention and is a cross-sectional view showing a solid-state image sensing device and a light-emitting diode which constitute an imaging module.
Figure 3B:
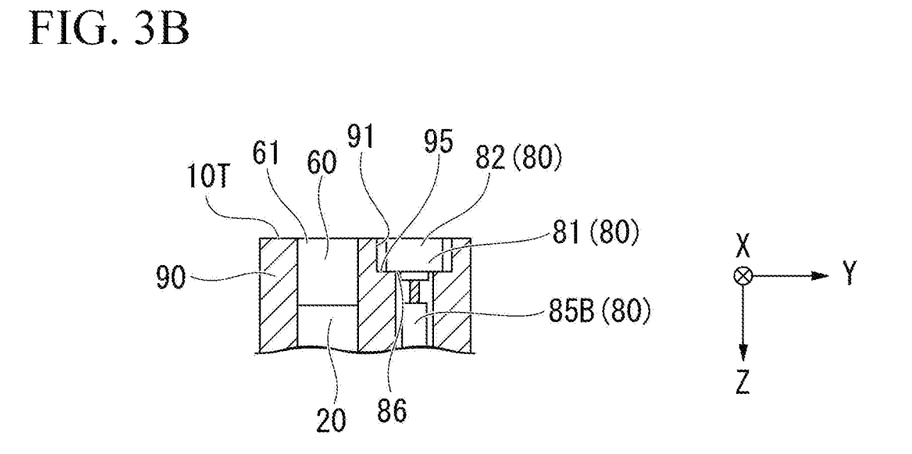
FIG. 3B is a view showing a relevant part of an endoscope according to a modified example 3 of one or more embodiments of the present invention and is a cross-sectional view showing a solid-state image sensing device and a light-emitting diode which constitute an imaging module.

FIGS. 3A and 3B are views showing relevant parts of endoscopes according to modified examples of the aforementioned embodiments and are cross-sectional views showing the lens unit 60, the light-emitting diode 80, and the light-shielding member 90 which constitute the imaging module 10 as seen in the X-direction.

The modified examples 2 and 3 show configurations in which the light-emitting diode 80 is disposed adjacent to the lens unit 60.

FIGS. 3A and 3B show the lens unit 60, the light-emitting diode 80, and the light-shielding member 90. The other members which are shown in FIG. 1 and constitute the imaging module 10 are omitted in the modified examples.

In the modified example 2 shown in FIG. 3A, a butt joint portion 95 is provided inside the light guiding hole 91 of the light-shielding member 90. A lower face 86 of the light-emitting diode 80 that is inserted into the inside of the light guiding hole 91 from the front side of the light-shielding member 90 is in contact with the butt joint portion 95. The butt joint portion 95 and the light-emitting diode 80 are fixed by a known fixing member such as adhesive or the like.

The length (in Z-direction) of the light guiding hole 91 according to the modified example 2 is shorter than that of the light guiding hole 91 according to one or more embodiments shown in FIG. 2. Inside the light guiding hole 91, the position of the light-emitting face 82 in the Z-direction is displaced from the end face 10T of the imaging module 10 to the inside of the light guiding hole 91.

The light guide plate 96 is provided on the light-emitting face 82. According to the configuration, similar to the above-mentioned modified example 1, it is possible to shorten the rigid-portion length L of the imaging module including the light-emitting diode 80. Additionally, it is possible to protect the light-emitting diode 80 by the light guide plate 96.

The modified example 3 shown in FIG. 3B is different from the modified example 2 in that the light guide plate 96 is not used. The other configurations of the modified example 3 are the same as those of the modified example 2.

In the Z-direction, the light-emitting face 82 coincides with the imaging surface 61 of the lens unit 60, that is, coincides with the end face 10T of the imaging module 10.

According to the configuration, similar to the above-mentioned modified example 1, it is possible to shorten the rigid-portion length L of the imaging module including the light-emitting diode 80. Furthermore, since light is emitted from the light-emitting face 82 at a wide angle, it is possible to illuminate the imaging object with it.

In other cases, although the modified examples 2 and 3 show the configurations in which the light-emitting diode 80 is disposed adjacent to the lens unit 60, the light-emitting diode 80 may be disposed adjacent to the solid-state image sensing device 20.

Modified Examples 4 and 5

Figure 4A:
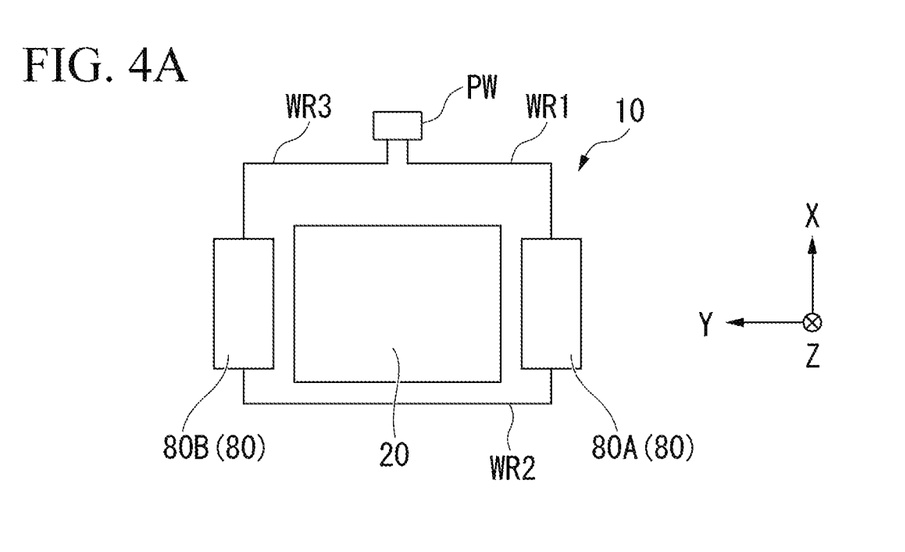
FIG. 4A is a view showing a relevant part of an endoscope according to a modified example 4 of one or more embodiments of the present invention and is a plan view showing a solid-state image sensing device and a light-emitting diode which constitute an imaging module.
Figure 4B:
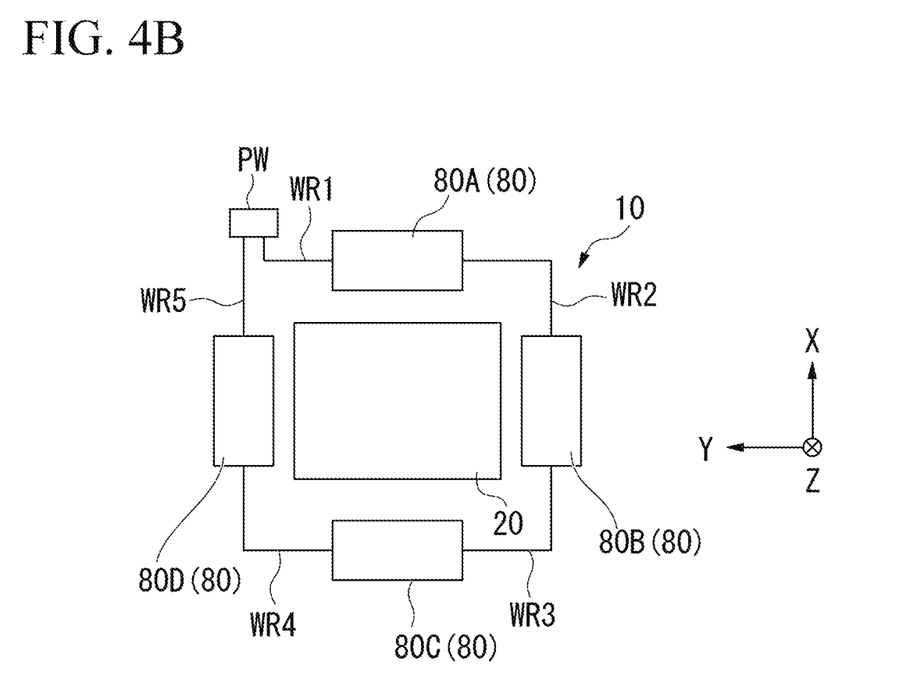
FIG. 4B is a view showing a relevant part of an endoscope according to a modified example 5 of one or more embodiments of the present invention and is a plan view showing a solid-state image sensing device and a light-emitting diode which constitute an imaging module.

FIGS. 4A and 4B are views showing relevant parts of endoscopes according to modified examples of the aforementioned embodiments and are plan views showing the solid-state image sensing device 20 and the light-emitting diode 80 which constitute the imaging module 10 as seen in the Z-direction.

FIGS. 4A and 4B show the solid-state image sensing device 20 and the light-emitting diode 80. The other members which are shown in FIG. 1 and constitute the imaging module 10 are omitted in the modified examples.

Note that, FIGS. 4A and 4B shows wirings WR (WR1, WR2, WR3, WR4, and WR5) connected to a plurality of light-emitting diodes and a power supply PW that supplies electric power to a plurality of light-emitting diodes.

In the modified example 4 shown in FIG. 4A, light-emitting diodes 80A and 80B are disposed at the right and the left of the solid-state image sensing device 20, respectively. In other words, the two light-emitting diodes 80A and 80B are disposed are so as to sandwich the solid-state image sensing device 20 in the Y-direction.

The power supply PW is connected to the first light-emitting diode 80A with the wiring WR1 interposed therebetween. The first light-emitting diode 80A is connected to the second light-emitting diode 80B with the wiring WR2 interposed therebetween. The second light-emitting diode 80B is connected to the power supply PW with the wiring WR3 interposed therebetween.

That is, the first light-emitting diode 80A and the second light-emitting diode 80B are series-connected to the power supply PW.

With this configuration, it is possible to supply a larger amount of light to the imaging module 10 than that of the configuration in which one light-emitting diode 80 is provided in the imaging module 10 as shown in FIG. 2. By applying this configuration to the endoscope 100, it is possible to further brightly illuminate an imaging object. Moreover, since the first light-emitting diode 80A and the second light-emitting diode 80B are series-connected to the power supply PW, it is possible to reduce the number of wirings less than that of parallel connection.

In the modified example 5 shown in FIG. 4B, the light-emitting diodes 80A, 80B, 80C, and 80D are disposed at the right, left, top, and bottom of the solid-state image sensing device 20. In other words, the two light-emitting diodes 80A and 80B are disposed are so as to sandwich the solid-state image sensing device 20 in the Y-direction, and the two light-emitting diodes 80C and 80D are disposed are so as to sandwich the solid-state image sensing device 20 in the X-direction. That is, the solid-state image sensing device 20 is surrounded by the periphery of the light-emitting diodes 80A, 80B, 80C, and 80D.

The power supply PW is connected to the first light-emitting diode 80A with the wiring WR1 interposed therebetween. The first light-emitting diode 80A is connected to the second light-emitting diode 80B with the wiring WR2 interposed therebetween. The second light-emitting diode 80B is connected to the third light-emitting diode 80C with the wiring WR3 interposed therebetween. The third light-emitting diode 80C is connected to the fourth light-emitting diode 80D with the wiring WR4 interposed therebetween. The fourth light-emitting diode 80D is connected to the power supply PW with the wiring WR5 interposed therebetween. That is, the light-emitting diodes 80A, 80B, 80C, and 80D are series-connected to the power supply PW.

With this configuration, it is possible to supply a larger amount of light to the imaging module 10 than that of the configuration in which the two light-emitting diodes 80A and 80B are provided in the imaging module 10 as shown in FIG. 4A. By applying this configuration to the endoscope 100, it is possible to further brightly illuminate an imaging object. Additionally, since the light-emitting diodes 80A, 80B, 80C, and 80D are series-connected to the power supply PW, it is possible to reduce the number of wirings less than that of parallel connection.

Modified Example 6

Figure 5:
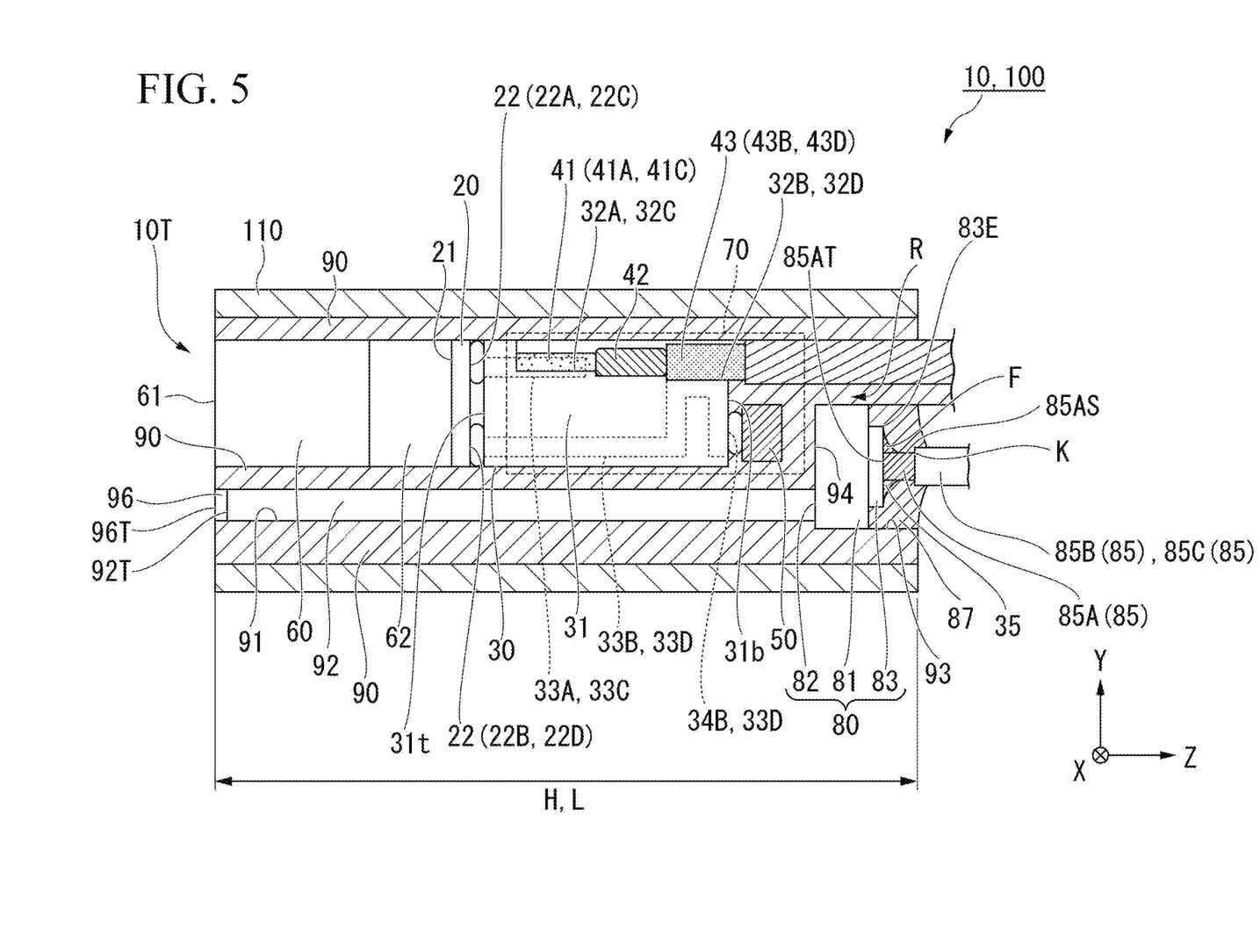
FIG. 5 is a view showing a relevant part of the endoscope according to a modified example 6 of one or more embodiments of the present invention and a cross-sectional view showing the configuration of the imaging module.

FIG. 5 is a view showing a relevant part of the endoscope according to a modified example of the aforementioned embodiments and is a cross-sectional view showing the configuration of the imaging module as seen in the X-direction.

As shown in FIG. 5, the imaging module 10 has a configuration in which the outside of the light-shielding member 90 is covered with a housing 110. The length of the housing 110 in the Z-direction is shorter than that of the rigid-portion length L. As a material of the housing 110, a material with biological compatibility may be selected. For example, stainless steel, aluminum, titanium, or ceramic such as alumina or zirconia may be used.

Inside the housing 110, the inner surface of the housing 110 comes into contact with the light-shielding member 90 and is fixed thereto. In the above-described configuration, since the housing 110 is used, resistance to an external force such as bending is improved. Moreover, a gap between the inner surface of the housing 110 and the light-shielding member 90 is filled with resin, and the imaging module 10 may be fixed by the resin.

In the imaging module according to the modified example 6, the same effects as the effects obtained by the aforementioned embodiments are obtained, and it is possible to achieve the imaging module 10 having a high degree of strength.

Catheter 200

Figure 6:
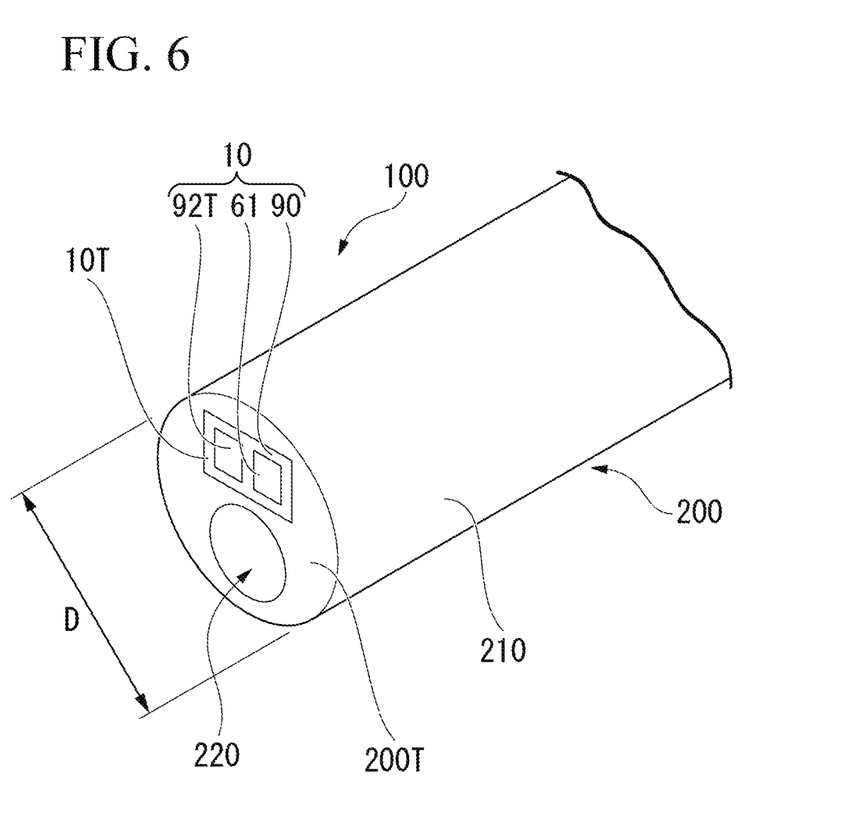
FIG. 6 is a perspective view showing a relevant part of a catheter according to one or more embodiments of the present invention.

FIG. 6 is a perspective view showing a relevant part of a catheter 200 according to the one or more embodiments of the present invention. In FIG. 6, identical symbols are used for the elements which are identical to those of one or more embodiments, and the explanations thereof are omitted or simplified here.

The catheter 200 shown in FIG. 6 is an imaging-module-attached catheter including the above-mentioned imaging module 10.

The catheter 200 includes a tube 210 that is made of, for example, silicon or the like and has an insulation property. In one or more embodiments, silicon is adopted as a material used to form the tube 210, a flexible material or a metal material other than silicon may be used.

For example, as a flexible material, silicon, polyurethane, polyethylene, polytetrafluoroethylene (PTFE, for example, Teflon (registered trademark)), or the like is adopted. As a metal material, titanium, a titanium alloy, a stainless steel, or the like is adopted. Additionally, it is not limited to a flexible material or a metal material, and ceramic material may be used as a material used to form the tube 210.

The endoscope 100 including the above-mentioned imaging module 10 according to one or more embodiments and a channel 220 are provided inside the tube 210. That is, the tube 210 encloses the imaging module 10.

At an end face 200T of the catheter 200, an opening 220T of the channel 220 opens, and the end face 10T of the imaging module 10 is exposed. That is, the end face 92T of the light guide 92, the end face of the light-shielding member 90, and the imaging surface 61 of the lens unit 60 are exposed at the end face 200T. In one or more embodiments, a realizable diameter D of the catheter 200 is, for example, approximately 2 mm.

The channel 220 may be used as a lumen and may be used as a working channel. In the case of using the channel 220 as a lumen, for example, a solvent medium injection lumen that ejects a solvent medium toward the front of the catheter 200 or a vacuuming lumen that removes liquid present in front of the catheter 200 can be provided in the tube 210.

Additionally, in the case of using the channel 220 as the working channel, for example, a treatment tool may be inserted into the channel 220. As the treatment tool, for example, various forceps, a snare, a guide wire, a stent, a laser treatment tool, a high-frequency treatment tool, or the like is adopted.

According to the above-described embodiments, since the endoscope 100 with a small diameter described in the above-mentioned embodiments is provided in the catheter 200, the same effects as the effects obtained by the aforementioned embodiments are obtained, and it is possible to achieve the catheter 200 that has a small diameter and is provided with both the channel 220 and the imaging module.

While embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENCE NUMERALS

10 . . . imaging module, 10T . . . end face, 20 . . . solid-state image sensing device, 21 . . . light-receiving face, 22, 22A, 22B, 22C, 22D . . . image-sensing terminal, 30 . . . connector, 31 . . . main body, 31b . . . lower face, 31t . . . upper face, 32A, 32B, 32C, 32D . . . side-face terminal, 33A, 33C . . . first implanted conductor (implanted conductor), 33B, 33D . . . second implanted conductor (implanted conductor), 34B, 34D . . . lower face terminal, 35 . . . solder, 40 . . . coaxial cable, 40F . . . first coaxial cable (coaxial cable), 40S . . . second coaxial cable (coaxial cable), 41, 41A, 41C . . . internal conductor, 42 . . . coating portion, 43, 43B, 43D . . . sheath conductor, 50 . . . capacitor, 60 . . . lens unit, 61 . . . imaging surface, 62 . . . cover member, 70 . . . insulating tube, 80 . . . light-emitting diode, 80A . . . first light-emitting diode, 80B . . . second light-emitting diode, 80C . . . third light-emitting diode, 80D . . . fourth light-emitting diode, 81 . . . light emitter, 82 . . . light-emitting face, 83 . . . light-emitter terminal, 83E . . . terminal outer periphery, 85 . . . power supply cable, 85A . . . electrical wire, 85AT . . . electrical-wire front end, 85AS . . . side surface portion, 85B . . . outer coating, 85C . . . shield member (shield), 86 . . . lower face, 87 . . . cable reinforcing portion, 90 . . . light-shielding member (light shield), 91 . . . light guiding hole, 92 . . . light guide, 92T . . . end face, 93 . . . light-emitting diode insertion hole, 94, 95 . . . butt joint portion, 96 . . . light guide plate, 96T . . . end face, 100 . . . endoscope, 110 . . . housing, 200 . . . catheter, 200T . . . end face, 210 . . . tube, 220 . . . channel, 220T . . . opening, F . . . curved surface, H . . . rigid portion, K . . . boundary, L . . . rigid-portion length, PW . . . power supply, R . . . rear region, WR, WR1, WR2, WR3, WR4, and WR5 . . . wiring

The invention claimed is:

1. An imaging module comprising:
a planar light emitter that comprises a light-emitting face and a light-emitter terminal;
a power supply cable that is connected to the light-emitter terminal and that supplies electric power to the planar light emitter;
a solid-state image sensing device that captures an image of an illumination object that is irradiated with light emitted from the light-emitting face;
a coaxial cable that is electrically connected to the solid-state image sensing device;
a light shield that is disposed between the solid-state image sensing device and the planar light emitter;
a light guide that guides light emitted from the light-emitting face to an outside of the imaging module; and
a connector that is disposed between the solid-state image sensing device and the coaxial cable and that comprises:

a main body formed of an insulator; and
an implanted conductor that is disposed inside the main body and that electrically connects the solid-state image sensing device to the coaxial cable, wherein
the planar light emitter, the solid-state image sensing device, part of the light shield, and the light guide constitute a rigid portion of the imaging module.

2. The imaging module according to claim 1, wherein
the connector includes a side-face terminal at which the implanted conductor is exposed to an inside of a groove formed on a side face of the main body,
the coaxial cable is electrically connected to the side-face terminal, and
the planar light emitter is adjacent to the coaxial cable in a rear region of the imaging module at a rear of the connector, the rear region facing the coaxial cable.

3. An imaging module comprising:
a planar light emitter that comprises a light-emitting face and a light-emitter terminal;
a power supply cable that is connected to the light-emitter terminal and that supplies electric power to the planar light emitter;
a solid-state image sensing device that captures an image of an illumination object that is irradiated with light emitted from the light-emitting face;
a coaxial cable that is electrically connected to the solid-state image sensing device;
a light shield that is disposed between the solid-state image sensing device and the planar light emitter; and
a light guide that guides light emitted from the light-emitting face to an outside of the imaging module, wherein
the planar light emitter, the solid-state image sensing device, part of the light shield, and the light guide constitute a rigid portion of the imaging module,
the power supply cable includes an electrical wire connected to the light-emitter terminal, and
a front end of the electrical wire contacts the light-emitter terminal, and solder covers a contact portion between the light-emitter terminal and the front end of the electrical wire.

4. The imaging module according to claim 3, wherein
the light-emitter terminal includes a terminal outer periphery at an end of the light-emitter terminal,
the electrical wire includes a side surface portion disposed apart from the front end of the electrical wire, and
the solder coats the light-emitter terminal and the electrical wire and forms a curved surface that extends from the terminal outer periphery toward the side surface portion.

5. The imaging module according to claim 3, wherein the power supply cable includes a shield that coats an outer side of the electrical wire.

6. The imaging module according to claim 3, wherein the power supply cable is an ultrafine coaxial cable.

7. An imaging module comprising:
a planar light emitter that comprises a light-emitting face and a light-emitter terminal;
a power supply cable that is connected to the light-emitter terminal and that supplies electric power to the planar light emitter;
a solid-state image sensing device that captures an image of an illumination object that is irradiated with light emitted from the light-emitting face;
a coaxial cable that is electrically connected to the solid-state image sensing device;
a light shield that is disposed between the solid-state image sensing device and the planar light emitter; and
a light guide that guides light emitted from the light-emitting face to an outside of the imaging module, wherein
the planar light emitter, the solid-state image sensing device, part of the light shield, and the light guide constitute a rigid portion of the imaging module, and
the light-emitter terminal and the power supply cable are coated with a cable reinforcing portion.

8. The imaging module according to claim 1, wherein the light shield is formed of a material that has a light shielding property.

9. The imaging module according to claim 1, further comprising a light guide plate disposed on an end face of the light guide.

10. The imaging module according to claim 1, wherein an end face of the light guide coincides with an end face of the imaging module.

11. The imaging module according to claim 1, further comprising a plurality of the planar light emitters that sandwich the solid-state image sensing device in plan view.

12. The imaging module according to claim 1, further comprising a plurality of the planar light emitters that surround the solid-state image sensing device in plan view.

13. The imaging module according to claim 1, further comprising a housing that covers an outer side of the light shield.

14. An endoscope comprising the imaging module according to claim 1.

15. A catheter comprising:
the imaging module according to claim 1; and
a tube that:
surrounds the imaging module,
has an insulation property, and
comprises a channel.

16. The imaging module according to claim 3, further comprising:
a lens unit that causes reflected light from the illumination object to be formed as an image on a light-receiving face of the solid-state image sensing device, wherein
the planar light emitter is adjacent to one of the lens unit and the solid-state image sensing device.

17. The imaging module according to claim 7, further comprising:
a lens unit that causes reflected light from the illumination object to be formed as an image on a light-receiving face of the solid-state image sensing device, wherein
the planar light emitter is adjacent to one of the lens unit and the solid-state image sensing device.

* * * * *